United States Patent [19]

Huber et al.

[11] Patent Number: 4,991,610

[45] Date of Patent: Feb. 12, 1991

[54] RINSING LIQUID APPARATUS FOR ANALYTICAL INSTRUMENTS

[76] Inventors: Bernhard Huber, Hildegardring 42, D-7770 Überlingen; Toma Tomoff, Lavendelweg 9, 7770 Überlingen, both of Fed. Rep. of Germany

[21] Appl. No.: 10,352

[22] Filed: Feb. 3, 1987

[30] Foreign Application Priority Data

Feb. 6, 1986 [DE] Fed. Rep. of Germany ....... 3603632

[51] Int. Cl.$^5$ ............................................... B08B 3/04
[52] U.S. Cl. ........................... 134/169.00 R; 134/195; 134/201; 220/380
[58] Field of Search ...................... 422/62, 100, 63, 81; 134/169 R, 94, 195, 201; 222/380, 375; 417/443

[56] References Cited

U.S. PATENT DOCUMENTS

| | | | |
|---|---|---|---|
| 1,946,473 | 2/1934 | Babendreer et al. | 222/383 X |
| 2,509,279 | 5/1950 | Sisson | 117/7 |
| 2,721,466 | 10/1955 | Nash | 68/176 |
| 3,138,015 | 6/1964 | Avery | 422/81 X |
| 3,205,825 | 9/1965 | Kojabashian | 103/50 |
| 3,572,130 | 3/1971 | Goldsmith | 422/100 X |
| 3,666,420 | 5/1972 | Paatzsch | 422/81 |
| 3,982,899 | 9/1976 | Kelm | 422/100 X |
| 4,111,051 | 9/1978 | Tamm et al. | 73/864.12 |
| 4,229,413 | 10/1980 | Marteau d'Autry | 422/100 |
| 4,318,884 | 3/1982 | Suzuki | 422/100 |
| 4,338,286 | 7/1982 | Ambers et al. | 422/81 |
| 4,457,184 | 7/1984 | Shiono | 422/100 |
| 4,640,821 | 2/1987 | Modo et al. | 422/81 |
| 4,664,391 | 5/1987 | Barra | 277/17 Y |

FOREIGN PATENT DOCUMENTS 2507260 2/1975 Fed. Rep. of Germany .
3535669 10/1985 Fed. Rep. of Germany .

Primary Examiner—Frankie L. Stinson
Attorney, Agent, or Firm—Thomas P. Murphy; Edwin T. Grimes

[57] ABSTRACT

The present application is directed to new and improved apparatus for use in analytical instruments which includes an elongated dosing tube having a tip at one end which is constructed and arranged to move between a sample vessel, a rinsing vessel and an analytical instrument; the other end of the dosing tube being connected in fluid flow communication to a rinsing liquid supply vessel through a sample pump assembly and a rinsing liquid pump assembly; the liquid pump assembly including a pump cylinder having an inlet and an outlet; a pump piston arranged for reciprocal movement in the pump cylinder between a first end position in the discharge direction and an opposite second end position in the intake direction; a first check valve mounted on the inlet of the pump cylinder and a second check valve mounted on the outlet of the pump cylinder; a seal mounted adjacent the outlet which cooperates with the pump piston to sealingly close the outlet when the pump piston is positioned in its first end position in the discharged direction.

2 Claims, 1 Drawing Sheet

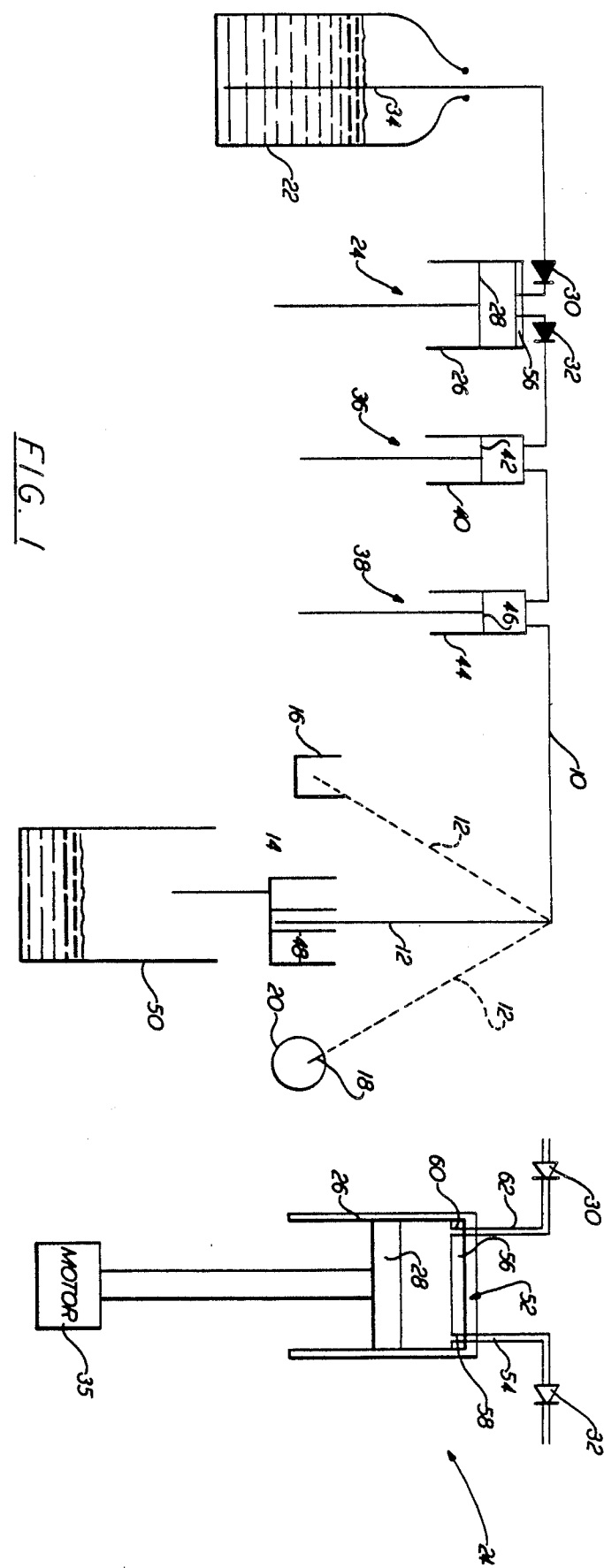

RINSING LIQUID APPARATUS FOR ANALYTICAL INSTRUMENTS

FIELD OF INVENTION

This invention relates to analytical instruments and more particularly to rinsing liquid apparatus used in combination with an analytical instrument.

BACKGROUND OF INVENTION

U.S. Pat. No. 4,111,051 describes method and apparatus for sample feeding systems utilized in flameless atomic absorption spectroscopy, in which a sample is withdrawn from a sample vessel by a dosing tube and then the dosing tube is moved to an atomizing device, e.g. a graphite tube atomizer and the sample is dispensed therein. The other end of the dosing tube communicates with a sample pump and with a rising fluid pump for delivery in one direction only. A rinsing process is employed between the individual dosing processes if successively different samples are dosed, wherein the free end or tip of the dosing tube is dipped into a rinsing vessel. Rinsing liquid is pumped by the rinsing liquid pump from a rinsing liquid container through the dosing tube into the rinsing vessel, which is formed as an overflow vessel, whereby the tip of the dosing tube is rinsed on its inside as well as on its outside. The dosing tube is filled with rinsing liquid and a small air volume is taken in by the sample pump or a separate air pump after the dosing tube has been lifted out of the rinsing vessel. Then the tip of the dosing tube is guided to a sample vessel and a well-defined sample volume is taken in by means of the sample pump. This sample volume is supplied to the atomizing device by a return stroke of the sample pump. A return stroke of the air pump ejects at least a part of the air volume taken in, whereby residue of the sample liquid is blown off the wall of the dosing tube.

The rinsing liquid pump comprises a pump cylinder having an inlet and an outlet. A pump piston is arranged in the pump cylinder, which is movable by a servomotor between a first end position in the discharge direction and a second opposite end position in the intake direction. One check valve is arranged on the inlet side and a second check valve is arranged on the outlet side of the pump cylinder. Rinsing liquid is taken in through the check valve in the pump cylinder on the inlet side with the intake stroke of the pump piston. This rinsing liquid is forced into the dosing tube through the check valve on the outlet side during the subsequent discharge stroke.

Very small sample volumes are dosed with such devices which, for example, is very desirable in flameless atomic absorption spectroscopy. It is very important that these sample volumes be observed very exactly, because atomic absorption spectroscopy is a quantitative measuring method, and depends on the quantity of atoms of a looked for element in a cloud of atoms generated in the graphite tube and as a result, an error in the dosed sample volume directly and substantially affects the end results.

Similar problems also appear in the high pressure liquid chromatography.

It has been found that the test results are sometimes inconsistent when employing the above described testing methods. It is one object of the present invention to avoid these measuring errors.

One of the aspects of the invention is based on the discovery that the described measuring errors are due to leakages of the check valves in the rinsing liquid pump. Such check valve leakage can be caused in the outlet of the rinsing liquid pump by particles in the rinsing liquid. Also, the surface tension of the rinsing liquid can affect the valve. These leakages become more apparent when the dosed sample volume is small.

SUMMARY OF THE INVENTION

Briefly the foregoing and other objects of the invention are realized by the provision of new and improved apparatus for use in analytical instruments, which include an elongated dosing tube having a tip at one end that is constructed and arranged to move between a sample vessel, a rinsing vessel and an analytical instrument, and the other end thereof being connected in fluid flow communication to a rinsing liquid supply vessel through a sample pump assembly and a rinsing liquid pump assembly. The liquid pump assembly includes a pump cylinder having an inlet and an outlet, a pump piston that has been arranged for reciprocal movement in the pump cylinder, and motive means for moving the pump piston in the pump cylinder between a first end position in the discharge direction and an opposite second end position in the intake direction. A first check valve is mounted on the inlet side of the pump cylinder and a second check valve is mounted on the outlet side of the pump cylinder. Sealing means are mounted adjacent the outlet which cooperate with the pump piston to sealingly close the outlet when the pump piston is positioned in its first end position in the discharge direction.

According to one aspect of the invention the sealing means adjacent the outlet comprises a sealing disc disposed at the outlet side of the internal end face of the pump cylinder, and the pump piston is constructed and arranged to sealingly engage the sealing disc when in its first end position. The sealing disc has a through bore communicating with the outlet.

According to another aspect of the invention, the disc extends over the whole internal end face of the pump cylinder, and a second through bore is provided which communicates with the inlet.

There has thus been outlined rather broadly the more important features of the invention in order that the detailed description thereof that follows may be better understood and in order that the present contribution to the art may be better appreciated. There are, of course, additional features of the invention which will be described hereinafter and which will form the subject of the claims appended hereto. Those skilled in the art will appreciate that the conception upon which the disclosure is based may readily be utilized as a basis for the designing of other systems for carrying out the several purposes of the invention. It is important, therefore, that the claims be regarded as including such equivalent systems as do not depart from the spirit and scope of the invention.

Several embodiments of the invention have been chosen for purposes of illustration and description and are shown in the accompanying drawings, forming a part of the specification.

BRIEF DESCRIPTION OF THE DRAWINGS

FIG. 1 is a schematic view, which illustrates the construction of a device for dosing liquids in an analyzing apparatus in which a rinsing liquid pump is used; and FIG. 2 is an enlarged side elevation showing the construction of the rinsing liquid pump.

DETAILED DESCRIPTION OF THE PRESENTLY PREFERRED EMBODIMENTS

In FIG. 1, numeral 10 designates a dosing tube which has a pivotable tip or free-end 12 that is successively movable by an actuating mechanism into a rinsing vessel 14, a sample vessel 16 and into a dosing opening 18 of an analytical instrument 20. The dosing tube and the actuating mechanism can be constructed in the manner described in detail in U.S. Pat. No. 4,111,051, which description is incorporated herein by reference. The dosing tube 10 communicates with a rinsing liquid vessel 22 through a rinsing liquid pump indicated at 24. The rinsing liquid pump 24, as best seen in FIG. 2, comprises a pump cylinder 26, in which a pump piston 28 is guided, and check valves 30 and 32 mounted in the inlet and the outlet, respectively. The inlet of the rinsing liquid pump 24 is connected to a conduit 34, FIG. 1, extending to the bottom of the rinsing liquid container 22. The piston 28 of the rinsing liquid pump 24 is movable by motive means such as a servomotor 35 between an upper first end position for discharge and a lower second end position for intake, as viewed in FIG. 2. A relatively large rinsing liquid volume is taken in from the rinsing liquid container 22 and is delivered through the dosing tube 10 with each stroke of the pump piston 28, delivery being in only one direction from the left side to the right side as viewed in FIG. 1.

Referring to FIG. 1, an air pump 36 and a sample pump 38 are connected to the section of the dosing pump which is always filled with rinsing liquid on the outlet side of the rinsing liquid pump. Both, the air pump 36 and the sample pump 38, pump only rinsing liquid and consequently can not retain residue of preceding samples, and thus cannot cross-contaminate the next sample. The air pump has a cylinder 40 in which a piston 42 is movable. A relatively small liquid volume is removed from the dosing tube 10 and is returned thereto during a complete stroke of the piston 42. The sample pump 38 comprises a cylinder 44 in which a piston 46 is movable. Also in this case, a relatively small liquid volume is taken from the dosing tube and is returned thereto during a complete stroke of the piston 42.

The rinsing vessel 14 has an overflow 48 communicating with a waste vessel 50.

At the beginning of each dosing cycle, the dosing tube 10 is positioned with its free end or tip 12 in the rinsing vessel 14. The piston 28 of the rinsing liquid pump 24 moves upwardly so that rinsing fluid flows through the dosing tube 10 to the right as viewed in FIG. 1 and cleans it from sample residue and contamination. When the system is totally filled with rinsing liquid, i.e. up to the top of the overflow 48, then the tip 12 is moved out of the rinsing vessel. The piston 42 of the air pump 36 is moved downwardly and the air pump 36 takes in, for example, 10 microliters of rinsing liquid so that the rinsing liquid column in the dosing tube 10 retracts and a corresponding volume of air is taken in at the tip 12. Thereafter, the tip 12 is inserted in the sample vessel 16. The piston 36 of the sample pump 38 moves downwardly and takes in, for example, 20 microliters of rinsing liquid out of the dosing tube 10. That results in drawing-in a corresponding volume of sample liquid. This sample liquid is separated from the rinsing liquid by an air bubble. As the next step, the tip 12 of the dosing tube 10 is moved to the analytical instrument 20, the tip 12 entering the dosing opening 18. Then, the pistons 46 and 42 are moved upwardly one after the other to expel the sample liquid as well as the air bubble. Thereafter, the pump piston 28 of the rinsing liquid pump 24, controlled by a control device, moves downwardly to its end position in the intake direction to bring in new rinsing liquid through the check valve 30.

As illustrated more clearly in FIG. 2, additional or supplemental sealing means indicated at 52 are provided in series with the outlet 54. This sealing means cooperates with the pump piston 28 to completely shut off the outlet 54 when the pump piston 28 is in its upper first end position.

The sealing means 52 comprises a sealing disc 56 arranged on the outlet side of the internal end face of the pump cylinder 26. The pump piston 28 sealingly engages this sealing 56 when it is in its upper first end position. A bore 58 extends through the sealing disc 56 and communicates with the outlet 54. In the illustrated preferred embodiment, the sealing disc 56 extends over the whole end face of the pump cylinder 26, and a second bore 60 is provided in the sealing disc 56, which communicates with the inlet 62.

It will thus be seen that, in addition to the check valve 32, the outlet 54 is sealingly shut off by the pump piston 28 which engages the sealing disc 56 and the sealing the bore 58 when the pump piston 28 is in its upper first position. As a result dosing errors are prevented, which might be due to check valve leakages.

The sealing can also be effected by other means, such as for example, by a sealing cone arranged on the pump piston instead of the sealing disc described.

Although specific embodiments have been illustrated and described, it will be obvious to those skilled in the art that various modifications may be made without departing from the spirit and scope of the invention which is to be limited solely by the appended claims.

What is claimed is:

1. Apparatus for use in analytical instruments comprising, in combination:

an elongated dosing tube having a tip at one end, said tip being constructed and arranged to move between a sample vessel, a rinsing vessel and an analytical instrument; the other end of said dosing tube being connected in fluid flow communication to a rinsing liquid supply vessel through a sample pump assembly and a rinsing liquid pump assembly; said liquid pump assembly including a pump cylinder having an inlet and an outlet; a pump piston arranged for reciprocal movement in the pump cylinder; motive means for moving said pump piston in said pump cylinder between a first end position in the discharge direction and an opposite second end position in the intake direction; a first check valve mounted on said inlet of said pump cylinder and a second check valve mounted on said outlet of said pump cylinder; sealing means mounted adjacent said outlet which cooperate with said pump piston to sealingly close said outlet when said pump piston is positioned in its first end position in the discharge direction, said sealing means comprising a sealing disc disposed at the outlet side of the internal end face of the pump cylinder, said pump piston being constructed and arranged to sealingly engage said sealing disc when in its first end position, and said sealing disc having a thru bore communicating with said outlet.

2. Apparatus for use in analytical instruments comprising, in combination:

an elongated dosing tube having a tip at one end, said tip being constructed and arranged to move between a sample vessel, a rinsing vessel and an analytical instrument; the other end of said dosing tube being connected in fluid flow communication to a rinsing liquid supply vessel through a sample pump assembly and a rinsing liquid pump assembly; said liquid pump assembly including a pump cylinder having an inlet and an outlet; a pump piston arranged for reciprocal movement in the pump cylinder; motive means for moving said pump piston in said pump cylinder between a first end position in the discharge direction and an opposite second end position in the intake direction; a first check valve mounted on said inlet of said pump cylinder and a second check valve mounted on said outlet of said pump cylinder; sealing means mounted adjacent said outlet which cooperate with said pump piston to sealingly close said outlet when said pump piston is positioned in its first end position in the discharge direction, said sealing means comprising a sealing disc disposed at the outlet side of the internal end face of the pump cylinder, said pump piston being constructed and arranged to sealingly engage said sealing disc when in its first end position, said sealing disc having a first thru bore communicating with said outlet, said disc extends over the whole internal end face of the pump cylinder, and said sealing disc having a second thru bore communicating with said inlet.

* * * * *